US009340479B2

(12) United States Patent
Dahlberg

(10) Patent No.: US 9,340,479 B2
(45) Date of Patent: May 17, 2016

(54) METHODS OF SYNTHESIZING ALPHA ACIDS AND SUBSTANTIALLY ENANTIOMERICALLY PURE COMPOSITIONS THEREOF

(71) Applicant: KINDEX PHARMACEUTICALS, INC., Seattle, WA (US)

(72) Inventor: Clinton Dahlberg, Port Orchard, WA (US)

(73) Assignee: KINDEX PHARMACEUTICALS, INC., Seattle, WA (US)

( * ) Notice: Subject to any disclaimer, the term of this patent is extended or adjusted under 35 U.S.C. 154(b) by 0 days.

(21) Appl. No.: 14/596,094

(22) Filed: Jan. 13, 2015

(65) Prior Publication Data

US 2015/0197472 A1   Jul. 16, 2015

Related U.S. Application Data

(60) Provisional application No. 61/926,824, filed on Jan. 13, 2014.

(51) Int. Cl.
| | |
|---|---|
| *C07C 45/46* | (2006.01) |
| *C07C 45/29* | (2006.01) |
| *C07C 45/51* | (2006.01) |
| *C07C 45/62* | (2006.01) |
| *C07C 45/67* | (2006.01) |
| *C07C 45/68* | (2006.01) |

(52) U.S. Cl.
CPC ............ *C07C 45/294* (2013.01); *C07C 45/46* (2013.01); *C07C 45/512* (2013.01); *C07C 45/62* (2013.01); *C07C 45/673* (2013.01); *C07C 45/68* (2013.01); *C07B 2200/07* (2013.01); *C07C 2101/10* (2013.01); *C07C 2101/16* (2013.01)

(58) Field of Classification Search
CPC .......... C07C 45/46; C07C 45/52; C07C 45/71
USPC ................................................. 568/347, 379
See application file for complete search history.

(56) References Cited

U.S. PATENT DOCUMENTS

| 4,053,517 A | 10/1977 | Reininger et al. |
| 5,767,319 A | 6/1998 | Ting et al. |

OTHER PUBLICATIONS

Clarke, B., et al., "The isomerization of humulone I. isolation of photoisohumulone," J. Inst. Brew 71: 26-36 (1965).
Desai, A., et al., "META060 inhibits multiple kinases in the NF-Kb pathway and suppresses LPS—mediated inflammation in vitro and ex vivo," Inflammation research 58: 229-234 (2009).
Donnelly, W., et al.,"Cis-and trans-Tetrahydroisohumulones," J. Chem. Soc. 524-530 (1970).
Drewett, K.G., et al., "Chemistry of hop constituents, part XXXVI, and improved synthesis of hop B-Acids (Lupulones)," J. Brew Inst. Brew 76: 188-190 (1970).
Everard, A., et al., "Tetraydro iso-Alpha acids from hops improve glucose homeostatis and reduce body weight gain and metabolic endotoxemia in high-fat diet-fed mice,"; PLos one vol. 7, Issue 3: e33858 (2012).
Hay, B., et al., "Efficient one-step preparation of the beer additive Tetrahydroiso alpha-acids," Journal of agriculture and food chemistry, 39: 1732-1734 (1991).
Hayerick, A., et al., "Photolysis of hop-derived trans-iso-alpha-acids and transtetrahydroiso-alpha-adds," Photochem Photobiol Sci. 2: 306-14 (2003).
Honig, L., et al., "National Hop Report" NASS(2012).
Huvaere, K., et al., "Photooxidative degradation of beer bittering principles: A key step on the route to lightstruck flavor formation in beer," J. Agric. food Chem., 53: 1489-1494 (2005).
Intelmann, D., et al. "O stable isotope labeling, quantitative model experiments, and molecular dynamic simulation studies on the trans-specific degradation of the bitter tasting Iso-a-acids of beer," J. Agric. Food Chem. 57: 11014-11023 (2009).
Jaskula, B., et al., "A kenetic study on the isomerization of hop alpha-acids," Journal of agriculture and food chemistry 56: 6408-6415 (2008).
Jones, J., et al., "A Mediterranean-style low glycemic-load diet improves variables of metabolic syndrome in women, and addition of a phytochemical-rich medical food enhances benefits on lipoprotein metabolism," Journal of Clinical Lipidology 5: 188-196 (2011).
Khatib, A., et al., "Isolation of individual hop iso-alpha-acids stereoisomers by beta-cyclodextrin," Food chemistry 119: 354-357 (2010).
Koller, H., "Magnesium ion catalyzed isomerization of humulone; A new route to pure isohumulones," J. Inst. Brew 75: 175-179 (1969).
Laws, D.R.J., et al., Chemistry of hop constituents. Part XXXVII. Separation and characterization of cis- and trans-Isohumulone and deduction of absolute con-figurations, J. of Chem. Soc. 2412-2415 (1971).
Nozawa, H., et al., "Inhibitory effects of beer on heterocyclic amine-induced mutagenesis and PhIP-induced aberrant crypt foci in rat colon." Mutation research 559: 177-187 (2004).
Nozawa, H., et al., Intake of beer inhibits azoxymethane-induced colonic carcinogenesis in male fischer 344 rats., Int. J. Cancer 108: 404-411 (2004).
Nozawa, H., et al. "Dietary supplement of isohumulones inhibits the formation of aberrant crypt foci with a concomitant decrease in prostaglandin E2 level in rat colon," Mol. Nutr. Food Res. 49: 772-778 (2005).
Nozawa, H., et al. "Inhibition of PhIP-induced mammary carcinogenesis in female rats by ingestion of freeze dried beer," Cancer Letters vol. 235, Issue 1: 121-129 (2006).
Sierksma, A., et al., "Effect of moderate alcohol comsumption on adiponectin, tumor necrosis factor-alpha, and insulin sensitivity," Daibetes care vol. 27:(1) (2004).

(Continued)

Primary Examiner — Sikarl Witherspoon
(74) Attorney, Agent, or Firm — Perkins Coie LLP; Patrick Morris

(57) ABSTRACT

Methods of synthesizing a cis 3,4-dihydroxy-2-(3-methylbutanoyl)-5-(3-methylbutyl)-4-(4-methylpentanoyl)cyclopent-2-en-1-one ("KDT500") derivative are provided. Such methods may be used to synthesize any desired KDT derivative. In one embodiment, the KDT500 derivative is KDT501.

27 Claims, 4 Drawing Sheets

(56) References Cited

OTHER PUBLICATIONS

Ting, P., et al., "Preparation and purification of hop acids and their dervatives," Journal of society of brewing chemist 54(2): 103-109 (1996).

Ting, P., et al., "Thermal isomerization of cohumulone," Journal of American society of brewing chemist 67: 152-156 (2009).

Tripp, M., et al., "Subjects with elevated LDL cholesterol and metabolic syndrome benefit from supplementation with soy protein, phytosterols, hops rho iso-alpha acids, and Acacia nilotica proanthocyanidins," Journal of clinical lipidology 4: 59-68 (2010).

Tyrrell, E., et al., "Structure elucidation and an investigation into the in vitro effects of hop acids on human cancer cells," Photochemistry Letters 3: 17-23 (2010).

Urban, J., et al. "Absolute configuaration of beer's bitter compounds," Angew. Chem. Int. 52: 1553-1555 (2013).

Vezerle, M., et al., "The absolute configuration of the isohumulones and the humulinic acids," 27: 4939-4945 (1971).

Verzele, M., et al., "Development in Food Science;" Preface VII-VIII (1991).

Wang, G., et al., "Terpene biosynthesis in glandular trichomes of hop," Plant physol. 148: 1254-166 (2008).

Weiss, A., et al., "Sensory and analytical characterization of reduced, isomered hop extracts and their influence and use in beer," J. Inst. Brew 108(2), 236-242 (2002).

Xiao, Li, et al., "First total synthesis of Kenusanone B," Synthetic communications 28(15), 2861-2869 (1998).

Yajima, H., et al., "Isohumulones, bitter acids derived from hops, activate both peroxisome proliferator-activated receptor a and y and reduce insulin resistance," Journal of biological chemistry 279: 33456-33462 (2004).

A.

B.

| # | Name | CH$_2$CHC(CH$_3$)$_2$ | H |
|---|---|---|---|
| 3 | | R$_1$ | R$_2$, R$_3$, R$_4$ |
| 4 | Deoxyhumulone | R$_1$, R$_2$ | R$_3$, R$_4$ |
| 5 | Lupulone | R$_1$, R$_2$, R$_3$ | R$_4$ |
| 6 | | N/A | R$_1$, R$_2$, R$_3$, R$_4$ |

METHODS OF SYNTHESIZING ALPHA ACIDS AND SUBSTANTIALLY ENANTIOMERICALLY PURE COMPOSITIONS THEREOF

PRIORITY CLAIM

This application claims priority to U.S. Provisional Application No. 61/926,824, filed Jan. 13, 2014, which is incorporated herein by reference.

BACKGROUND

Numerous publications have demonstrated that beer and the bitter acids found in beer are beneficial to health. As such, light-stable reduced hops bitter acid extracts have been used to help treat or prevent various conditions such as diabetes, cancer, inflammation, and obesity. The female cones of *Humulus lupulus* L. (hops) produce a mixture of humulones and lupulones known as alpha- and beta-acids, respectively. The group of alpha-acids used as the main bittering agent in conventional commercial brewing methods, known as the reduced iso-alpha-acids, are thought to be responsible for many of the beneficial effects of beer.

There are several categories of reduced iso-alpha-acids, each existing naturally as a mixture of congeners and stereoisomers, and each having independent biological activity. The categorization depends on the location and degree of saturation. The class of compounds resulting from the reduction of only the C6 carbonyl to a hydroxyl is collectively referred to as the rho iso-alpha-acids (RIAAs). Compounds where only both isoprenyl moieties are saturated are referred to as tetrahydro iso-alpha-acids (THIAAs). In addition to the existence of cis and trans diastereomers, there are a variety of congeners within each of the three classes as a result of the incorporation of various short-chain fatty acids into the biosynthetic pathway of the corresponding phloroglucinols (Wang, 2008). The phloroglucinols are common precursors to the alpha-acids that are precursors to iso-alpha-acids, which are in turn precursors to the reduced iso-alpha-acids.

Among other biological activities, mixtures of reduced iso-alpha-acids have been shown to inhibit the activity of several enzymes (e.g., spleen tyrosine kinase, Bruton's tyrosine kinase, phosphatidylinositol 3-kinase), inhibit osteoclastogenesis, reduced arthritis index, decreased bone, joint and cartilage degradation, reduce IL-6 levels, inhibit prostaglandin E2 production, inhibit inducible cyclooxygenase-2 protein expression, and reduce NFκB translocation and abundance. However, the heterogeneity of the mixtures prevents a clear understanding of the relationships between each of the congeners and stereoisomers present with respect to their individual and relative biological activities. As such, synthesis of enantiomerically pure reduced iso-alpha-acids is desired to ensure accurate biological analysis and structure-function relationships.

Most commercial routes of synthesis are dependent upon natural extracts of the alpha- and beta-acids found in hops for a starting material, and result in products of varying purity. Notwithstanding the purity of products produced using natural extracts, these routes of synthesis also present challenges with respect to the availability and sourcing of starting materials due to time, cost, and agricultural variability. As such, there is a need for methods that can produce enantiomerically pure reduced iso-alpha-acids for use in pharmaceutical compositions and treatments, which also address the issues discussed above related to the starting materials.

A total synthesis of the iso-alpha-acids from phloroglucinol that was previously described in the literature suffered from low yields and produced only racemic material (Ting, 2009). The development of a commercially viable, robust total synthesis of the iso-α-acids would allow labeling and chemical derivatization of the hops bitter acids to enable further investigation of biological structure-activity relationships (SAR) and would support pharmaceutical development. However, there are three steps within the total synthesis of the iso-α-acids from phloroglucinol where a large percentage of an undesired product can result, including prenylation, oxidation (undesired enantiomer) and isomerization (undesired diastereomer). Likewise, the synthesis of iso-alpha-acids from natural hops extracts also produces undesired product, which contributes to low yields. Therefore, there is a need to optimize the methods of synthesis from natural hop extracts and precursors, such as phloroglucinols, to prepare enantiomerically pure or substantially enantiomerically pure reduced iso-alpha-acid compounds and their derivatives for use in pharmaceutical compositions and treatments.

SUMMARY

According to the embodiments described herein, methods of synthesizing a cis 3,4-dihydroxy-2-(3-methylbutanoyl)-5-(3-methylbutyl)-4-(4-methylpentanoyl)cyclopent-2-en-1-one ("KDT500") derivative are provided. Such methods may be used to synthesize any desired KDT derivative. In one embodiment, the KDT500 derivative is KDT501.

In certain embodiments, the methods of synthesizing a KDT500 derivative may include a step of acylating a starting material in the presence of a Friedel Crafts catalyst to produce a product A. In one aspect, the starting material is phloroglucinol and the product A is acylphloroglucinol. The method further includes steps of prenylating the product A in the presence of a strong aqueous base to produce a mixture of beta acids; performing an acidic hydrogenation on the mixture of beta-acids (e.g., deoxyhumulone, lupulone, compound (6), or a combination thereof) to produce tetrahydrodeoxyhumulone and reacting the tetrahydrodeoxyhumulone with strong oxidation conditions to produce a product B. In one aspect, the strong oxidation conditions include sulfuric acid and hydrogen peroxide; and product B is tetrahydrohumulone. The method further includes steps of performing an isomerization of the product B to produce one or more diastereomers of tetrahydroisohumulone; and purifying the one or more diastereomers of tetrahydroisohumulone by one or more of a salt crystallization, counter-current chromatography (CCC) purification, and chiral chromatography.

In other embodiments, the methods of synthesizing a KDT500 derivative may include a step of performing a thermal isomerization on a starting material to produce a mixture of cis and trans diastereomers of isohumulone. In one aspect, the starting material is an alpha-acid derived from a hops CO2 extractant (e.g., (−)-humulone). The method further includes steps of isolating the cis diastereomers from the mixture of cis and trans diastereomers of isohumulone by precipitating the trans diastereomers of isohumulone; performing a hydrogenation on the cis diastereomers of isohumulone to produce a mixture of cis and trans diastereomers of tetrahydroisohumulone; and purifying the one or more diastereomers of tetrahydroisohumulone by one or more of a salt crystallization, counter-current chromatography (CCC) purification, and chiral chromatography.

In some embodiments, the methods described above may also include a step of performing an epimerization of the trans diastereomers of tetrahydroisohumulone using one or more weak sterically non-hindered bases (e.g., DMAP, DABCO, imidazole, isoquinoline, 4-picoline, pyridine, substituted pyridines, NMM, sodium acetate, or tetralkylammonium acetates) to produce cis and trans diastereomers of tetrahydroisohumulone.

In other embodiments, the methods of synthesizing a KDT500 derivative may include steps of performing a photoisomerization on a starting material to produce trans diastereomers of isohumulone; performing an epimerization of the trans diastereomers of isohumulone to produce cis and trans diastereomers of tetrahydroisohumulone; and purifying the one or more diastereomers of tetrahydroisohumulone by one or more of a salt crystallization, CCC purification, and chiral chromatography.

BRIEF DESCRIPTION OF THE DRAWINGS

FIG. 1A illustrates a Friedel-Crafts acylation performed on phloroglucinol (1) to produce acylphloroglucinol (2) in accordance with some embodiments. Acylphloroglucinol (2) was over-prenylated in the presence of potassium hydroxide to produce a mixture of beta-acids including (3), deoxyhumulone (4), lupulone (5), and (6) (also see FIG. 1B for 3-6). An acidic hydrogenation in the presence of gaseous hydrogen ($H_2$) and palladium on carbon (Pd/C) was performed on the mixture of deoxyhumulone (4), lupulone (5), and (6) to form tetrahydrodeoxyhumulone (7). Oxidation of tetrahydrodeoxyhumulone (7) under strong oxidation conditions produced tetrahydrohumulone (8) in high yield. Thermal isomerization of tetrahydrohumulone (8) in the presence of alkali earth metals produced tetrahydroisohumulone (9). Finally, purification via countercurrent chromatography (CCC), chiral chromatography and potassium salt crystallization was used to produce the final product, a potassium salt of cis 3,4-dihydroxy-2-(3-methylbutanoyl)-5-(3-methylbutyl)-4-(4-methylpentanoyl)cyclopent-2-en-1-one ("KDT500"), called KDT510 (10). FIG. 1B shows the generic chemical structure that defines the class of beta-acids which may be produced as a result of the prenylation of acylphloroglucinol (2). The functional groups of the various beta-acids including (3), deoxyhumulone (4), lupulone (5), and (6) are listed in the table.

DETAILED DESCRIPTION

Figure 1:
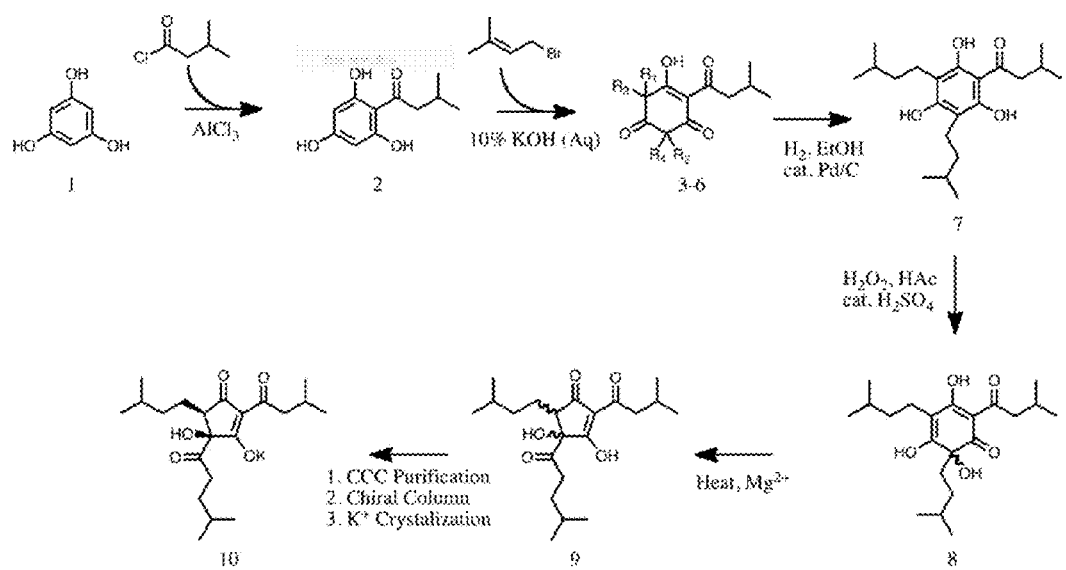
FIG. 1 illustrates the representative scheme and intermediates for the synthesis of KDT501 (10) from phloroglucinol (1).
Figure 1:
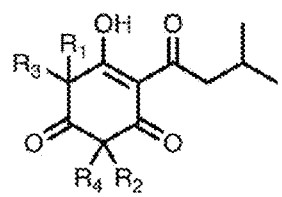

Methods for the synthesis of iso-alpha-acids and iso-alpha-acid derivatives are disclosed herein. In some embodiments, the iso-alpha-acids and iso-alpha-acid derivatives may be cis 3,4-dihydroxy-2-(3-methylbutanoyl)-5-(3-methylbutyl)-4-(4-methylpentanoyl)cyclopent-2-en-1-one ("KDT500") derivatives and substantially enantiomerically pure compositions and pharmaceutical compositions comprising these derivatives.

In certain embodiments, the KDT500 derivatives that are synthesized by the methods provided herein are selected from (+)-(4S,5R)-3,4-dihydroxy-2-(3-methylbutanoyl)-5-(3-methylbutyl)-4-(4-methylpentanoyl)cyclopent-2-en-1-one ("(+)-KDT500") having the structure set forth in Formula I, (−)-(4R,5S)-3,4-dihydroxy-2-(3-methylbutanoyl)-5-(3-methylbutyl)-4-(4-methylpentanoyl)cyclopent-2-en-1-one ("(−)-KDT500") having the structure set forth in Formula II, and salts and crystals thereof.

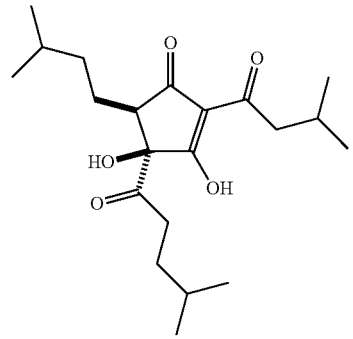

Formula I

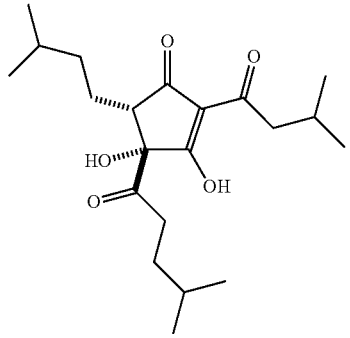

Formula II

In certain embodiments, the KDT500 derivatives that are synthesized by the methods provided herein are salts of (+)-KDT500 or (−)-KDT500. In certain embodiments, these derivatives may be inorganic or organic salts, including but not limited to potassium, aluminum, calcium, copper, guanidinium, iron, lithium, magnesium, sodium, zinc, cinchonidine, cinchonine, and diethanolamine salts of (+)-KDT500 or (−)-KDT500. In certain of these embodiments, the derivative may be a potassium salt of (+)-KDT500 having the structure set forth in Formula III ("(+)-KDT501").

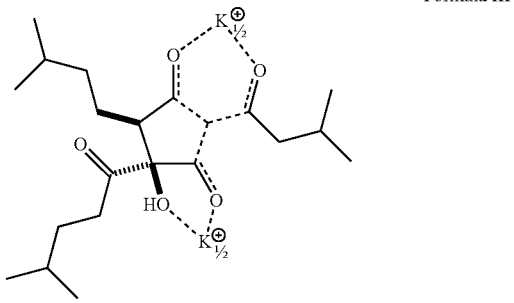

Formula III

In other embodiments, a KDT500 derivative as provided herein may be a salt of KDT500, including for example, KDT501.

In some embodiments, the synthesis methods produce enantiomerically pure or substantially enantiomerically pure KDT500 or derivatives thereof. For example, the synthesis methods may produce only (+)-KDT500 or derivatives thereof or only (−)-KDT500 or derivatives thereof. In other embodiments, the synthesis methods result in a mixture of enantiomeric forms of KDT500 derivatives. In these embodiments, one or more subsequent separation and/or purification steps may be performed to isolate a single enantiomeric form or to generate a substantially enantiomerically pure composition as provided herein. In certain embodiments, the synthesis methods produce KDT501.

Provided herein in certain embodiments are methods of synthesizing compositions comprising one or more of the KDT500 derivatives provided herein. In certain of these embodiments, the compositions are substantially enantiomerically pure. The term "substantially enantiomerically pure" as used herein refers to a composition in which 90% or more of a particular compound in the composition is in a first enantiomeric form, while 10% or less is in a second enantiomeric form. For example, in a substantially enantiomerically pure (+)-KDT500 composition, 90% or more of the KDT500 in the composition is (+)-KDT500 and 10% or less is (−)-KDT500. In certain embodiments, the "first enantiomeric form" of a compound includes salts and crystals of that enantiomeric form. For example, in a substantially enantiomerically pure (+)-KDT500 composition, 90% or more of the KDT500 in the composition is in the form of (+)-KDT500 or salts or crystals thereof, while 10% or less is in the form of (−)-KDT500 or salts or crystals thereof. In certain embodiments, a substantially enantiomerically composition may contain 91%, 92%, 93%, 94%, 95%, 96%, 97%, 98%, 99%, 99.5%, 99.9%, 99.95%, or 99.99% or greater of a first enantiomeric form of a compound.

In certain embodiments, methods of synthesizing compositions of (+)-KDT500 are provided. In certain of these embodiments, the compositions are substantially enantiomerically pure. In certain of these embodiments, a percentage of the (+)-KDT500 in the composition is in the form of salts or crystals of (+)-KDT500. In some of these embodiments, all of the (+)-KDT500 in the composition is in salt or crystal form. Thus, provided herein are methods of synthesizing substantially enantiomerically pure compositions of (+)-KDT500 salts or crystals. In other embodiments, none of the (+)-KDT500 in the composition is in salt or crystal form.

Provided herein in certain embodiments are methods of synthesizing KDT500 derivatives for use as a pharmaceutical compositions and one or more pharmaceutically acceptable carriers. In certain embodiments, the pharmaceutical compositions are substantially enantiomerically pure. In certain of these embodiments, the substantially enantiomerically pure pharmaceutical compositions comprise (+)-KDT500, (−)-KDT500, or salts or crystals thereof. A "pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. Such a carrier may comprise, for example, a liquid or solid filler, diluent, excipient, solvent, encapsulating material, stabilizing agent, or some combination thereof. Each component of the carrier must be "pharmaceutically acceptable" in that it must be compatible with the other ingredients of the composition and must be suitable for contact with any tissue, organ, or portion of the body that it may encounter, meaning that it must not carry a risk of toxicity, irritation, allergic response, immunogenicity, or any other complication that excessively outweighs its therapeutic benefits.

Examples of pharmaceutically acceptable carriers for use in the compositions provided herein include, but are not limited to, (1) sugars, such as lactose, glucose, sucrose, or mannitol; (2) starches, such as corn starch and potato starch; (3) cellulose and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) disintegrating agents such as agar or calcium carbonate; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; (21) paraffin; (22) lubricants, such as talc, calcium stearate, magnesium stearate, solid polyethylene glycol, or sodium lauryl sulfate; (23) coloring agents; (24) glidants such as colloidal silicon dioxide, talc, and starch or tri-basic calcium phosphate; and (24) other non-toxic compatible substances employed in pharmaceutical compositions such as acetone. In one embodiment, the pharmaceutically acceptable carrier used herein is an aqueous carrier, e.g., buffered saline and the like. In other embodiments, the pharmaceutically acceptable carrier is a polar solvent, e.g., acetone and alcohol.

Pharmaceutical compositions as provided herein may further comprise one or more pharmaceutically acceptable auxiliary substances as required to approximate physiological conditions. For example, compositions may comprise one or more pH adjusting agents, buffering agents, or toxicity adjusting agents, including for example sodium acetate, sodium chloride, potassium chloride, calcium chloride, sodium lactate, and the like.

Pharmaceutical compositions as provided herein may be formulated into a suitable dosage form, including for example capsules, cachets, pills, tablets, lozenges (using a flavored basis, usually sucrose and *acacia* or tragacanth), powders, granules, as a solution or a suspension in an aqueous or non-aqueous liquid, as an oil-in-water or water-in-oil liquid emulsion, as an elixir or syrup, or as pastilles (using an inert base, such as gelatin and glycerin, or sucrose and *acacia*)

and/or as mouth washes and the like, each containing a predetermined amount of a KDT500 derivative as an active ingredient. In certain embodiments, the compositions may be formulated as a time release delivery vehicle, such as for example a time release capsule. A "time release vehicle" as used herein refers to any delivery vehicle that releases active agent over a period of time rather than immediately upon administration. In other embodiments, the compositions may be formulated as an immediate release delivery vehicle.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a substantially enantiomerically pure mixture of the powdered KDT500 derivative or further moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of a KDT500 derivative therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain pacifying agents and may be of a composition that they release the KDT500 derivative(s) only, or preferentially, in a certain portion of the gastrointestinal tract, optionally, in a delayed manner. Examples of embedding compositions which can be used include polymeric substances and waxes. The KDT500 derivative can also be in micro-encapsulated form, if appropriate, with one or more of the above-described excipients.

The concentration of KDT500 derivatives in the compositions provided herein may vary. Concentrations may be selected based on fluid volumes, viscosities, body weight, and the like in accordance with the particular mode of administration selected and the biological system's needs. In certain embodiments, the concentration of a KDT500 derivative in a composition provided herein may be from about 0.0001% to 100%, from about 0.001% to about 50%, from about 0.01% to about 30%, from about 0.1% to about 20%, or from about 1% to about 10% wt/vol.

Further provided herein are methods of analyzing, synthesizing, purifying, and/or crystallizing the KDT500 derivatives provided herein, as well as methods of analyzing, synthesizing, purifying, and/or crystallizing the substantially enantiomerically pure KDT500 compositions provided herein.

In certain embodiments, the synthesis methods provided herein generate a single enantiomer of a KDT500 derivative. For example, the synthesis methods may generate only (+)-KDT500 or only (−)-KDT500. In other embodiments, the synthesis methods result in a mixture of enantiomeric forms of KDT500 derivatives. In these embodiments, one or more subsequent separation and/or purification steps may be performed to isolate a single enantiomeric form or to generate a substantially enantiomerically pure composition as provided herein.

Synthesis of KDT500 Derivatives from Phloroglucinol.

According to some embodiments, methods are provided herein for the synthesis of KDT500 or derivatives thereof using an organic compound as a starting material. In certain embodiments, the KDT500 derivative may be KDT501 (10). In some embodiments, the organic compound may be a benzenetriol compound, such as phloroglucinol (1) (see, e.g., Example 1 below and FIG. 1). The development of a commercially viable, robust total synthesis from organic compounds alleviates concerns about agricultural variability (Honig, 2012). Synthesis from this starting material would also allow labeling and chemical derivatization of the hops bitter acids to enable further investigation of biological structure-activity relationships (SAR) and would support pharmaceutical development. As provided herein, phloroglucinol (1) was chosen as the desired starting material for total synthesis of KDT501 (10) due to its general availability and easy sourcing. As detailed herein, numerous steps have been taken to improve the overall synthetic yield of KDT500 or derivatives thereof from phloroglucinol (1).

Previously, total synthesis of isohumulone (12) from phloroglucinol (1) suffered from low yields and produced only racemic material (Ting, 2009). Most commercial routes are dependent upon natural extracts of the alpha and beta-acids found in hops and result in varying purity. Thus, a total synthetic route of synthesizing KDT500 or derivatives thereof using phloroglucinol (1) as a starting material was optimized through novel improvements as described herein. According to the embodiments provided herein, the methods of synthesizing KDT500 or derivatives thereof may include one or more steps that includes, but is not limited to, acetylation, prenylation, hydrogenation, isomerization, epimerization, salt crystallization, countercurrent chromatography (CCC), and chiral chromatography.

(Acylation Step) According to some embodiments provided herein, methods of synthesizing KDT500 or derivatives thereof from phloroglucinol may include an acylation step. The acylation step includes acylating a starting material in the presence of a Friedel Crafts catalyst to produce an acylated product. In this way, the side-chain corresponding to the desired hops bitter acid congener may be installed in near quantitative yields using the appropriate Friedel Crafts acylation conditions (Reininger, 1977). For example, the starting material may be an organic compound such as phloroglucinol and the acylated product may be acylphloroglucinol (2). In some embodiments, under Friedel-Crafts acylation conditions, isovaleryl chloride may be introduced to phloroglucinol to produce acylphloroglucinol (2) (see FIG. 1A). In some embodiments, isovaleryl chloride may be introduced in greater than an 85% yield during the acylation step.

(Prenylation Step) In certain embodiments provided herein, methods of synthesizing KDT500 or derivatives thereof from phloroglucinol may include a prenylation step. The prenylation step may include prenylating an acylated product to produce a mixture of beta acids. In certain embodiments, the acylated product may be acylphloroglucinol (2) and the mixture of beta-acids produced may include one or more of the beta-acids shown in FIG. 1B such as: (3), deoxyhumulone (4), lupulone (5), and (6). The prenylation step, which includes a substitution reaction introducing an isoprenyl side chain, is a typical bottleneck in the total synthesis of any of the hops acids. Previously, the prenylation step has been performed by reacting acylophloroglucinol with excess 1-bromo-3-methylbut-2-ene in the presence of liquid ammonia, resulting in individual beta-acid yields of 50-70% (Drewett, 1970). However, in contrast to the previous literature, in some embodiments provided herein, the methods of synthesis of KDT500 or derivatives thereof include a prenylation step using an adapted aqueous potassium hydroxide procedure (Xiao, 1998) (see FIG. 1A). For example, in certain embodiments, the prenylation step may include prenylating the acylated product in the presence of potassium hydroxide to produce a mixture of beta-acids. This less selective aqueous reaction condition results in poor overall yields of beta-acids (isolated yields of any single beta-acid ranged from 20-30%). However, despite low yields, this reaction condition was specifically selected for in order to improve other downstream steps, such as hydrogenation, in the synthesis process.

Specifically, the downstream hydrogenation step as described herein was optimized for the use of the mixture of beta-acids comprising beta-acids deoxyhumulone (4), lupulone (5), and (6) with limited amounts of beta-acid (3). As a result, the objective at the prenylation step was to limit the amount of beta-acid (3) through over-prenylation of the acylated product, acylphloroglucinol (2). Accordingly, over-prenylation of acylphloroglucinol (2) resulted in the reaction being driven to lupulone (5) with the major side products being beta-acids deoxyhumulone (4) and (6). Thus, in certain embodiments, the prenylation step may include over-prenylating acylophloroglucinol (2) to produce a mixture of beta-acids. In certain embodiments, the over-prenylation may be performed by over-prenylating acylphloroglucinol (2) through addition of excess 1-bromo-3-methylbut-2-ene in the presence of potassium hydroxide to produce a mixture of beta-acids. In some embodiments, the mixture of beta-acids may include one or more of the beta-acids (3), deoxyhumulone (4), lupulone (5), and (6). In certain embodiments, the resulting amount of beta-acid (3) is limited. In some embodiments, deoxyhumulone (4) may be isolated in >90% homogeneity using differential pH extraction. In certain embodiments, lupulone (5) may be isolated in >95% homogeneity by crystallization in hexanes.

(Hydrogenation Step) According to some embodiments provided herein, methods of synthesizing KDT500 or derivatives thereof from phloroglucinol may include a hydrogenation step. In some embodiments, the hydrogenation step comprises performing a hydrogenation on the mixture of beta-acids to produce tetrahydrodeoxyhumulone (7) (see FIG. 1A). In some embodiments, the hydrogenation may be an acidic hydrogenation. In certain embodiments, the acidic hydrogenation is performed in the presence of gaseous hydrogen ($H_2$) and a catalyst. In certain embodiments, palladium on carbon (Pd/C) may be the catalyst. In other embodiments, other catalysts including, but not limited to, platinum, rhodium and ruthenium may be used to perform the acidic hydrogenation.

(Oxidation Step) According to some embodiments provided herein, methods of synthesizing KDT500 or derivatives thereof from phloroglucinol may include an oxidation step. Generally, the oxidation of deoxyhumulone (4) to produce humulone must be conducted carefully in deference to the unsaturation present on the isoprenyl groups. However, tetrahydrodeoxyhumulone (7) is more stable than deoxyhumulone (4) as the alkene bonds are all reduced; therefore, strong oxidation conditions may be employed in the methods described herein. As a result, the optimization of the oxidation step in the synthesis of KDT500 or derivatives thereof resulted in a high yield of tetrahydrohumulone (8). Thus, in certain embodiments, the oxidation step comprises reacting tetrahydrodeoxyhumulone (7) with strong oxidation conditions to produce tetrahydrohumulone (8) (see FIG. 1A). In some embodiments, the strong oxidation conditions comprise adding sulfuric acid and hydrogen peroxide to deoxyhumulone (4). In other embodiments, other strong oxidizing conditions include, but are not limited to, permanganate ($MnO_4^-$), chromium trioxide ($CrO_3$), dichromate ($Cr_2O_7^{2-}$), and osmium tetroxide ($OsO_4$).

(Isomerization Step) In some embodiments provided herein, methods of synthesizing KDT500 or derivatives thereof from phloroglucinol may include an isomerization step. The six-membered ring of tetrahydrohumulone (8) undergoes isomerization via ring-contraction to form the five-membered ring tetrahydroisohumulone (9), using either thermal or photo catalysis. Photoisomerization is stereospecific and produces only the trans diastereomers of tetrahydroisohumulone (9) (Clarke, 1965). In contrast, thermal isomerization, catalyzed by the presence of alkaline earth metals, is stereoselective and produces a mixture of both cis and trans diastereomers of tetrahydroisohumulone (9). Thus, in some embodiments, an isomerization step comprises performing an isomerization of tetrahydrohumulone (8) to produce tetrahydroisohumulone (9). In certain embodiments, the isomerization may be thermal isomerization, which may be catalyzed by alkali earth metals such as magnesium 2+. When thermal isomerization is used, a mixture of cis and trans diastereomers of tetrahydroisohumulone (9) may be produced. In certain embodiments, the isomerization may be photoisomerization and trans diastereomers of tetrahydroisohumulone (9) may be produced.

(Purification Step) In certain embodiments provided herein, methods of synthesizing KDT500 or derivatives thereof from phloroglucinol may include a purification step. In certain embodiments, the purification step may comprise purifying the cis and/or trans diastereomers of tetrahydroisohumulone (9) by a salt crystallization, countercurrent chromatography (CCC) purification, and/or chiral chromatography resulting in KDT500 or derivatives thereof. In certain embodiments, the KDT500 derivative is KDT501 (10). Additionally, other methods of purification may be used to further purify the cis and/or trans diastereomers of tetrahydroisohumulone (9) to produce KDT501 (10).

Synthesis of KDT500 Derivatives from Natural Alpha-acids.

Figure 2:
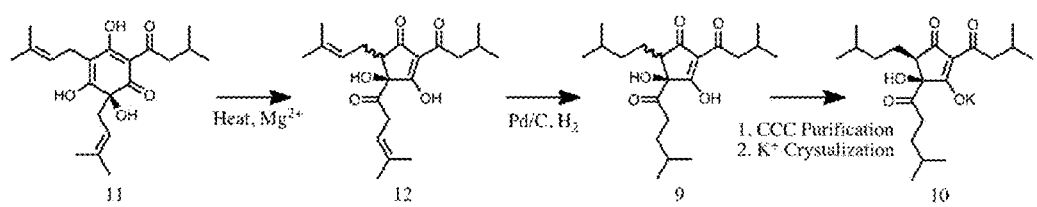
FIG. 2 illustrates the scheme for synthesis of enantioresolution and enantiopure (+)-KDT501 (10) from natural alpha-acids by the conventional hops bitter acid process according to some embodiments. An alkaline thermal isomerization of (−)-humulone (11) produced a mixture of cis and trans diastereomers of isohumulone (12), with the cis form being the predominant diastereomer produced. The cis diastereomers of isohumulone (12) were separated from the cis and trans diastereomer mixture through precipitation of the trans diastereomers. An acidic hydrogenation in the presence of gaseous hydrogen ($H_2$) and palladium on carbon (Pd/C) was performed on the cis diastereomers of isohumulone (12), which produced a mixture of cis and trans diastereomers of tetrahydroisohumulone (9). Finally, cis diastereomers were further purified from the trans diastereomers of tetrahydroisohumulone (9) by a salt crystallization, countercurrent chromatography (CCC) purification, and chiral chromatography resulting in the final product, KDT501 (10).

According to some embodiments, methods are provided herein for the synthesis of KDT500 or derivatives thereof from natural alpha-acids (see FIG. 2). In some embodiments, the KDT500 or derivatives thereof comprise enantioresolution and enantiopure (+)(−)KDT501 (10). The iso-alpha acid, isohumulone (12), is very structurally similar to tetrahydroisohumulone (9) with increased functionality due to the unsaturation present in the isoprenyl side chains. Conventionally, isohumulone (12) is prepared by isomerization of the alpha acid, (−)-humulone (11), which is known to be unstable and reactive due to increased electronic conjugation (Intelmann, 2009; Heyerick, 2003; and Huvaere, 2005). Synthetically, (−)-humulone (11) can be accessed through the oxidation of deoxyhumulones (4), but with variable yields and without stereoselectivity (Ting, 2009). The methods provided herein for the synthesis of KDT500 or derivatives thereof from natural alpha-acids may be used as a recycling step to improve overall yields. According to certain embodiments, the methods of synthesis of KDT500 or derivatives thereof from natural alpha-acids may include one or more steps including isolation of alpha-acids from a hops extract, isomerization, isolation of cis diastereomers, hydrogenation, epimerization, salt crystallization, CCC purification, and chiral chromatography.

(Isolation of Alpha-Acids) In certain embodiments, methods of synthesizing KDT500 or derivatives thereof from natural alpha-acids may include an isolation step wherein natural alpha-acids are isolated from a hops $CO_2$ extract. For example, a differential pH extraction of the hops $CO_2$ extract may be performed followed by countercurrent chromatography of the resulting natural alpha-acids. In certain embodiments, the resulting natural alpha-acids are (−)-humulone (11) (see FIG. 2). In one embodiment, the natural alpha-acids are optically active.

(Isomerization Step) In some embodiments provided herein, methods of synthesizing KDT500 or derivatives thereof from natural alpha-acids may also include an isomerization step. In certain embodiments, an isomerization step may include performing an isomerization of (−)-humulone (11) to produce a mixture of cis and trans diastereomers of isohumulone (12) (see FIG. 2). In some embodiments, the isomerization may be a thermal alkaline isomerization. The thermal alkaline isomerization may be catalyzed by alkali earth metals such as magnesium 2+. In certain embodiments, the cis diastereomer of isohumulone (12) is the diastereomer that is predominantly produced in an approximately 3:1 ratio (cis:trans) from the mixture of cis and trans diastereomers of isohumulone (12) after performing a thermal alkaline isomerization of (−)-humulone (11). In some embodiments, the isomerization may be a photoisomerization and the trans diastereomer of isohumulone (12) is produced.

(Isolation of Cis Diastereomers) According to some embodiments, methods of synthesizing KDT500 or derivatives thereof from natural alpha-acids may include an isolation step including isolating the cis diastereomers of isohumulone (12) from the trans diastereomers of isohumulone (12). For example, following thermal isomerization of (−)-humulone (11), a mixture of cis and trans diastereomers of isohumulone (12) are produced. In some embodiments, the isolation step may include precipitation of the trans diastereomers of isohumulone. The precipitation of the trans diastereomers of isohumulone may occur via a β-cyclodextrin complexation. For example β-cyclodextrin may be added to the mixture of cis and trans diastereomers of isohumulone (12) to precipitate the trans isohumulone according to the methods presented in Urban, 2013, which is hereby incorporated by reference in its entirety. In this way the trans diastereomers of isohumulone (12) form an aqueous insoluble precipitate which may be separated from the cis diastereomers of isohumulone (12) via centrifugation and decanting.

(Hydrogenation) According to certain embodiments, methods of synthesizing KDT500 or derivatives thereof from natural alpha-acids may also include a hydrogenation step. In certain embodiments, the hydrogenation step includes performing a hydrogenation on the cis diastereomers of isohumulone (12) to produce a mixture of cis and trans diastereomers of tetrahydroisohumulone (9) according to the methods presented in Urban, 2013, which is hereby incorporated by reference in its entirety (see FIG. 2). In some embodiments, the hydrogenation may be an acidic hydrogenation. In certain embodiments, the acidic hydrogenation is performed in the presence of gaseous hydrogen ($H_2$) and a catalyst. In certain embodiments, palladium on carbon (Pd/C) may be the catalyst.

(Purification Step) In some embodiments provided herein, methods of synthesizing KDT500 or derivatives thereof from natural alpha-acids may also include a purification step. As described previously, the purification step may comprise purifying the cis and trans diastereomers of tetrahydroisohumulone (9) by a salt crystallization, countercurrent chromatography (CCC) purification, and/or chiral chromatography (see FIG. 2). In some embodiments, the salt crystallization may be an aqueous potassium salt crystallization. Other methods may be used to further purify the cis and/or trans diastereomers of tetrahydroisohumulone (9) to produce enantioresolution and enantiopure (+)-KDT500 or derivatives thereof. In certain embodiments, the KDT500 derivative is KDT501 (10) and enantioresolution and enantiopure (+)-KDT501 is produced.

Epimerization of Trans-Diastereomers.

The process of synthesizing KDT500 or derivatives thereof from phloroglucinol (1) results in undesired trans diastereomers of tetrahydroisohumulone (9). Similarly, the process of synthesizing KDT500 or derivatives thereof from natural alpha-acids results in undesired trans diastereomers of isohumulone (12). As such, there is a need to improve the overall synthetic yield of KDT500 or derivatives thereof by recycling the undesired trans diastereomers to form the cis diastereomers, thus limiting any losses of product during synthesis from phloroglucinol (1) or natural alpha-acids.

Figure 3:
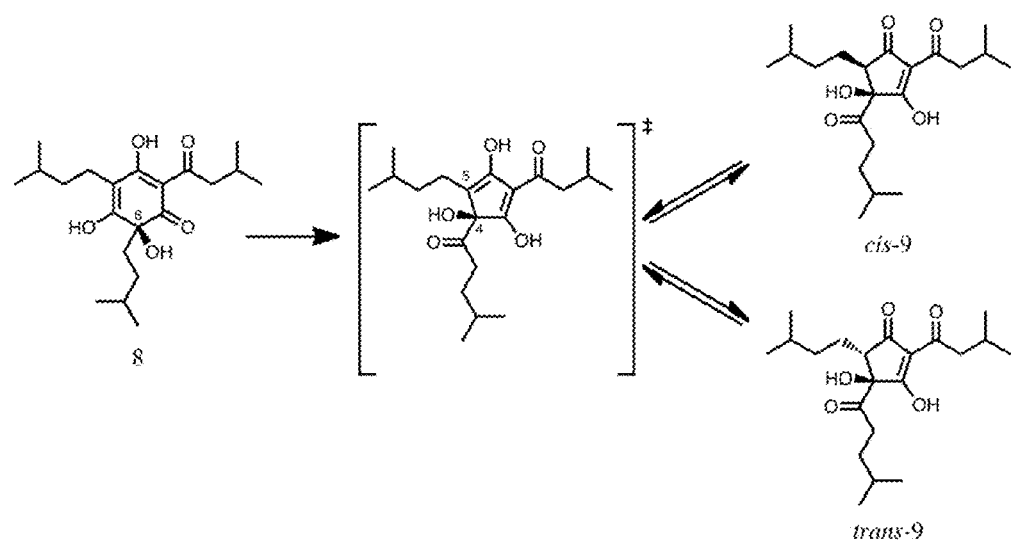
FIG. 3 illustrates the isomerization mechanism of tetrahydrohumulone (8) in accordance with some embodiments. The six-membered rings of tetrahydrohumulone (8) undergo isomerization via ring contraction to form the five membered rings of the cis and trans diastereomers of tetrahydroisohumulone (9). An enol intermediate that is present in the isomerization mechanism is shown in brackets.

The process of isomerization of tetrahydrohumulone (8) and (−)-humulone (11) involves contraction of the six-membered alpha-acid rings (through acyloin rearrangement) to form the five membered iso-alpha acid rings with two chiral centers, resulting in cis and/or trans diastereomers of tetrahydroisohumulone (9) and isohumulone (12), respectively. In 1970, a plausible isomerization mechanism of (−)-humulone (11) (or tetrahydrohumulone (8)) was proposed involving hydrogen bonding (Donnelly, 1970). However, in 1971, this mechanism was discarded (Laws, 1971) and replaced with one based upon an incorrect stereochemical assignment (Verzele, 1971). Recent absolute structure assignment of the hops bitter acids shows that the cis and trans diastereomers of tetrahydroisohumulone (9) and isohumulone (12) differ at C5, not C4 as previously reported (Urban 2013). More recently, the role of coordinating alkali earth metals as a catalyst to the isomerization has been formally recognized (Jaskula, 2008). As disclosed herein, the role of coordination between vicinal oxygen atoms of tetrahydrohumulone (8) (or (−)-humulone (11)) through an intermediate such as hydrogen or an alkali earth metal with an enol intermediate present in the isomerization mechanism was identified (see FIG. 3).

Optimization of the total synthesis of KDT501, a cis derivative of tetrahydroisohumulone (9), requires epimerization of the undesired trans diastereomer into the cis form. Previously, epimerization was thought to occur via retroisomerization to the six-membered ring (Verzele, 1991). However, as high temperatures are known to cause racemization of (−)-humulone (11) (Urban, 2013) and optical activity is retained, this mechanism is unlikely. As provided in Example 3 below, epimerization through an enol intermediate was shown to occur using tetrahydroisohumulone (9) and isohumulone (12). Therefore, in some embodiments, the methods of synthesizing, KDT500 or derivatives thereof from phloroglucinol (1) or natural alpha-acids as described herein may also include an epimerization step. As a result of this optimization, the undesired trans diastereomers can be recycled through the epimerization step, thus limiting any losses during synthesis.

According to some embodiments, the epimerization step may include epimerization of one or more trans diastereomers to form one or more cis diastereomers. Photo-induced isomerization is stereospecific and can be used to produce pure trans isomerized acids, whereas, thermal isomerization produces a mixture of both cis and trans diastereomers of the isomerized acids. Thus, in some embodiments, the epimerization step may be performed to recycle the trans diastereomers produced from either photo-induced isomerization or thermal isomerization. In certain embodiments, the trans diastereomers are from one or more of a member of the hops bitter acid family. For example, tetrahydroisohumulone (9) and isohumulone (12) may be members of the hops bitter acid family.

Figure 4:
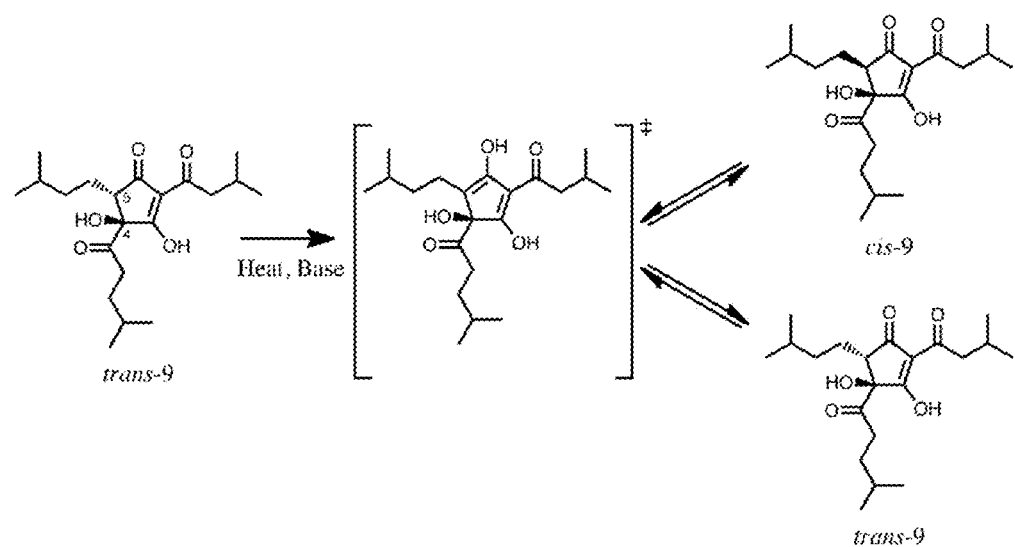
FIG. 4 illustrates the scheme for epimerization of pure trans diastereomers of tetrahydroisohumulone to a mixture of cis and trans diastereomers of tetrahydroisohumulone (9) in accordance with some embodiments. Addition of a weak, sterically non-hindered base formed a transitory enol intermediate for epimerization (the enol intermediate is shown in brackets).

In some embodiments, the epimerization step may be included as a step in the methods of synthesizing KDT500 or derivatives thereof from an organic compound such as phloroglucinol (1). For example, during synthesis of KDT500 or derivatives thereof from phloroglucinol (1), one or more trans diastereomers of tetrahydroisohumulone (9) is produced. Thus, in some embodiments, epimerization of one or more trans diastereomers of tetrahydroisohumulone (9) may be performed to form one or more cis diastereomers of tetrahydroisohumulone (9) (FIG. 4). Epimerization may be performed to abstract the hydrogen at C5, forming a transitory enol intermediate for epimerization while not causing racemization. Additionally, epimerization may occur through an enol intermediate and optical activity of the cis diastereomers may be preserved. In certain embodiments, epimerization of one or more trans diastereomers of tetrahydroisohumulone (9) may be performed using one or more weak, sterically non-hindered bases. For example, the one or more weak, sterically non-hindered bases may include DMAP, DABCO, imidazole, isoquinoline, 4-picoline, pyridine, substituted pyridines, NMM, sodium acetate, and tetralkylammonium acetates. In some embodiments, the sterically non-hindered bases may be in a pKa range of about 3-9. In certain embodiments, epimerization may be performed in a variety of solvents including diglyme, acetic acid, DMF and DMSO. In some embodiments, epimerization may be performed in a non-aqueous solvent including alcohol or ether. In certain embodiments, water may not be used as a solvent. According to some embodiments, epimerization may be performed under high temperatures. For example, epimerization may be performed under temperatures ranging from approximately 80° C.-120° C. In some embodiments, epimerization does not occur in the presence of alkali earth metals, such as magnesium.

In some embodiments, the epimerization step may be included as a step in the methods of synthesizing KDT500 or derivatives thereof from natural alpha-acids as described herein. For example, during synthesis of KDT500 or derivatives thereof from natural alpha-acids, one or more trans diastereomers of isohumulone (12) is produced. According to some embodiments, epimerization of one or more trans diastereomers of isohumulone (12) may be performed to form one or more cis diastereomers of isohumulone (12). Epimerization may be performed to abstract the hydrogen at C5, forming a transitory enol intermediate for epimerization. In certain embodiments, epimerization is performed under alkali conditions. In some embodiments, addition of boric acid to isohumulone (12) without further reduction promotes epimerization. In certain embodiments, epimerization may occur during an alkali borohydride reduction with heat.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Example 1

Synthesis of KDT501 from Phloroglucinol

A preliminary investigation into the total synthesis of KDT501 from phloroglucinol (1) is presented in FIG. 1A. Utilizing a Friedel-Crafts acylation, isovaleryl chloride was introduced in greater than an 85% yield to produce acylphloroglucinol (2). The substitution reaction introducing the isoprenyl side chain is a typical bottleneck in the total synthesis of any of the hops acids. Previously, the greatest selectivity seen in the literature produced lupulone (5) in a 73% yield, but required the use of liquid ammonia as the solvent. By contrast, the typical prenylation target, deoxyhumulone (4), has been reported in a 60% yield at best (Ting, 2009).

Recognizing the literature precedent for performing hydrogenolysis on lupulone (5) (Hay, 1991), less selective aqueous reaction conditions were chosen and the reaction was driven to lupulone (5) with the major side products being (6) and deoxyhumulone (4) (FIG. 1B); thus, limited amounts of beta-acid (3) was produced. An acidic hydrogenation was performed on this mixture producing tetrahydrodeoxyhumulone (7) as the major product from the greater mixture. As tetrahydrodeoxyhumulone (7) has had all alkene bonds reduced, strong peroxide conditions were used to produce tetrahydrohumulone (8) in high yield. A thermal isomerization of tetrahydrohumulone (8) was performed, producing a mixture of cis and trans diastereomers of tetrahydroisohumulone (9) in a 13% overall yield from phloroglucinol (1). Further purification via countercurrent chromatography (CCC), chiral chromatography and potassium salt crystallization was used to produce KDT501 (10).

Example 2

Synthesis of KDT501 from Natural Alpha-acids

Preliminary biological data was collected on KDT501 (10) formed through the conventional hops bitter acid process seen in FIG. 2. A differential pH extraction of a hops $CO_2$ extract, followed by CCC of the resulting alpha-acids enabled isolation of (−)-humulone (11). An alkaline thermal isomerization was employed to produce predominantly (~3:1) the cis diastereomer of isohumulone (12) from (−)-humulone (11). On gram scale syntheses of KDT501 (10), β-cyclodextrin was utilized to selectively encapsulate the trans diastereomers of isohumulone (12) (Khatib, 2010), forming an aqueous insoluble precipitate, which was removed via centrifugation and decanting. The cis-isohumulone (12) was converted into the magnesium salt and reduced via hydrogenation using a palladium on carbon catalyst. Following CCC purification of cis-tetrahydroisohumulone (9), an aqueous potassium salt crystallization was performed to provide additional enantio-resolution and enantiopure (+)-KDT501 (10).

Example 3

Epimerization of Trans-Diastereomers

The six-membered rings of tetrahydrohumulone (8) and (−)-humulone (11) undergo isomerization via ring-contraction to form the five-membered rings of tetrahydroisohumulone (9) and isohumulone (12), respectively, using either photoisomerization or thermal isomerization. In 1970, a plausible isomerization mechanism of tetrahydrohumulone (8) (or (−)- humulone (11)) was proposed involving hydrogen bonding (Donnelly, 1970), and was supported by an earlier paper recognizing the role of alkali earth metals in the isomerization (Köller, 1969). In 1971, a vicinal oxygen coordination mechanism was discarded (Laws, 1971) and replaced with one based upon steric control of structural assignment (Verzele, 1971). Therefore, in FIG. 3, the role of an enol intermediate present in the isomerization mechanism was reintroduced.

Epimerization of the trans diastereomers of the borohydride reduced derivatives of isohumulone (12) leads to only the cis diastereomer, with optical activity being retained (Ting, 1996). Previously, epimerization was thought to occur via retroisomerization to the six-membered ring (Verzele, 1991), but as high temperatures are known to cause racemization of (−)-humulone (11) (Urban, 2013) and optical activity is retained, this mechanism is unlikely. Thus, due to the interest of cis-tetrahydroisohumulone (9) as the major final product, isohumulone (12) and tetrahydroisohumulone (9) were tested to determine whether the entire hops bitter acid family may potentially epimerize through an enol intermediate. Whether boron could be the key component to abstracting the hydrogen of C5 to enable the epimerization under alkali conditions was tested by introducing boric acid to isohumulone (12) without further reduction. Though some epimerization appeared to be occurring, the bigger issue was the rate of decomposition of isohumulone (12) under these conditions.

Further epimerization work was performed using exclusively tetrahydroisohumulone (9) and weak sterically non-hindered to abstract the hydrogen at C5, forming a transitory enol intermediate for epimerization while not causing racemization. Epimerization can be performed in a wide variety of solvents (for example diglyme, acetic acid, and DMSO, but not water) using many bases, including: DMAP, DABCO, imidazole, isoquinoline, 4-picoline, and pyridine, at temperatures ranging from 80-120° C. As shown in FIG. 4, pure trans-9 was used to demonstrate the formation of cis-9 through an enol intermediate with optical activity preserved. Interestingly though, epimerization did not occur in the presence of alkali earth metals, such as magnesium, reinforcing previous observations during hydrogenation (Ting, 1998) that the alkali earth metals serve to protect the hops bitter acids from structural changes. The epimerization of tetrahydroisohumulone (9) was optimized in this discovery phase to form 3:1 mixtures of cis and trans diastereomers, respectively from purely trans starting material.

REFERENCES

The references, patents and published patent applications listed below, and all references cited in the specification above are hereby incorporated by reference in their entirety, as if fully set forth herein.

B. J. Clarke, R. P. Hildebrand, J. Inst. Brew 1965, 71, 26-36.
Desai, V. R. Konda, G. Darland, M. Austin, K. S. Prabhu, J. S. Bland, B. J. Carroll, M. L. Tripp, Inflammation Research 2009, 58, 229-234.
W. Donnelly, P. V. R. Shannon, J. Chem. Soc. C 1970, 524-530.
K. G. Drewett, D. R. J. Laws, Journal of the Institute of Brewing. Institute of Brewing (Great Britain) 1970, 76, 188-190.
A. Everard, L. Geurts, M. Van Roye, N. M. Delzenne, P. D. Cani, PloS one 2012, 7, e33858.
B. Hay, Journal of Agricultural and Food 1991, 39, 1732-1734.
A. Heyerick, Biochemistry 2001.
A. Heyerick, Y. Zhao, P. Sandra, K. Huvaere, D. De Keukeleire, F. Roelens, P. Sciences, E. Denis, S. Sciences, 0. Clie, et al., Photochem. Photobiol. Sci. 2003, 2, 306-314.
L. Honig, J. Garcia-Pratts, D. Flippin, F. Granja, C. Hawthorn, D. Losh, D. Norris, D. Schauber, E. White, National Hop Report (December 2012), 2012.
K. Huvaere, M. L. Andersen, L. H. Skibsted, A. Heyerick, D. De Keukeleire, Journal of agricultural and food chemistry 2005, 53, 1489-94.
D. Intelmann, O. Demmer, N. Desmer, T. Hofmann, Journal of agricultural and food chemistry 2009, 57, 11014-23.
B. Jaskula, P. Kafarski, G. Aerts, L. De Cooman, Journal of agricultural and food chemistry 2008, 56, 6408-15.
J. L. Jones, M. L. Fernandez, M. S. McIntosh, W. Najm, M. C. Calle, C. Kalynych, C. Vukich, J. Barona, D. Ackermann, J. E. Kim, et al., Journal of clinical lipidology 2011, 5, 188-96.
A. Khatib, E. G. Wilson, M. Supardi, R. Verpoorte, Food Chemistry 2010, 119, 354-357.
H. Köller, Journal of the Institute of Brewing 1969, 75, 175-179.
D. R. J. Laws, J. A. Elvidge, Journal of the Chemical Society C: Organic 1971, 2412.
R. H. Lerman, D. M. Minich, G. Darland, J. J. Lamb, J. Chang, A. Hsi, J. S. Bland, M. L.
H. Nozawa, A. Yoshida, O. Tajima, M. Katayama, H. Sonobe, K. Wakabayashi, K. Kondo, International journal of cancer. Journal international du cancer 2004, 108, 404-11.
H. Nozawa, K. Tazumi, K. Sato, A. Yoshida, J. Takata, S. Arimoto-Kobayashi, K. Kondo, Mutation research 2004, 559, 177-87.
H. Nozawa, W. Nakao, F. Zhao, K. Kondo, Molecular nutrition & food research 2005, 49, 772-8.
H. Nozawa, W. Nakao, J. Takata, S. Arimoto-Kobayashi, K. Kondo, Cancer letters 2006, 235, 121-9.
W. Reininger, A. Hartl, Method of Acylation of Phloroglucinol, 1977, U.S. Pat. No. 4,053,517.
A. Sierksma, H. Patel, N. Ouchi, S. Kihara, T. Funahashi, R. J. Heine, D. E. Grobbee, C. Kluft, H. F. J. Hendriks, Diabetes care 2004, 27, 184-9.
P. L. Ting, H. Goldstein, Journal of the American Society of Brewing Chemists 1996, 54, 103-109.
P. L. Ting, M. A. VanSanford, J. R. Refling, H. Goldstein, Preparation of Tetrahydroiso-alpha-acids by the Hydrogenation of the Metal Salts of Iso-alpha-acids, 1998, U.S. Pat. No. 5,767,319.
P. L. Ting, S. Kay, D. Ryder, J. Am. Soc. Brew. Chem 2009, 67, 152-156.
Tripp, Journal of Clinical Lipidology 2010, 4, 59-68.
E. Tyrrell, R. Archer, G. A. Skinner, K. Singh, K. Colston, C. Driver, Phytochemistry Letters 2010, 3, 17-23.
J. Urban, C. J. Dahlberg, B. J. Carroll, W. Kaminsky, Angewandte Chemie (International ed. in English) 2013, 52, 1553-5.
M. Verzele, D. De Keukeleire, Development in Food Science 1991, 27, 1-417.
M. Verzele, D. De Keukeleire, Tetrahedron 1971, 27, 4939-4945.
Wang Plant Physiol 148:1254 (2008).
A. Weiss, C. Schönberger, W. Mitter, M. Biendl, W. Back, M. Krottenthaler, Journal of the Institute of Brewing 2002, 108, 236-242.
L. Xiao, W. Tan, Synthetic communications 1998, 28, 2861-2869.

H. Yajima, E. Ikeshima, M. Shiraki, T. Kanaya, D. Fujiwara, H. Odai, N. Tsuboyama-Kasaoka, O. Ezaki, S. Oikawa, K. Kondo, The Journal of biological chemistry 2004, 279, 33456-62.

What is claimed is:

1. A method of synthesizing a cis 3,4-dihydroxy-2-(3-methylbutanoyl)-5-(3-methylbutyl)-4-(4-methylpentanoyl)cyclopent-2-en-1-one ("KDT500") derivative comprising:
    a) acylating a starting material comprising phloroglucinol (1) in the presence of a Friedel Crafts catalyst to produce a product A comprising an acylphloroglucinol;
    b) prenylating the product A in the presence of a strong aqueous base to produce a mixture of beta acids;
    c) performing an acidic hydrogenation on the mixture of beta-acids to produce tetrahydrodeoxyhumulone (7) and reacting the tetrahydrodeoxyhumulone (7) with strong an oxidation condition to produce a product B comprising tetrahydrohumulone (8);
    d) performing an isomerization of the product B comprising tetrahydrohumulone (8) to produce one or more diastereomers of tetrahydroisohumulone (9) comprising trans 3,4-dihydroxy-2-(3-methylbutanoyl)-5-(3-methylbutyl)-4-(4-methylpentanoyl)cyclopent-2-en-1-one;
    e) performing a thermal epimerization of trans 3,4-dihydroxy-2-(3methylbutanoyl)-5-(3-methylbutyl)-4-(4-methylpentanoyl)cyclopent-2-en-1-one in the presence of an alkaline earth metal; and
    f purifying the KDT500 and trans 3,4-dihydroxy-2-(3-methylbutanoyl)-5-(3-methylbutyl)-4-(4-methylpentanoyl)cyclopent-2-en-1-one respectively from step (e) by one or more of a salt crystallization, counter-current chromatography (CCC) purification, and chiral chromatography.

2. The method of claim 1, wherein KDT500 derivative is a potassium salt of KDT500.

3. The method of claim 1, wherein the strong aqueous base of step (b) comprises potassium hydroxide.

4. The method of claim 1, wherein the mixture of beta-acids comprises one or more beta-acids including (3), deoxyhumulone (4), lupulone (5), and (6).

5. The method of claim 4, wherein prenylating the product A comprises over-prenylating by the addition of excess 1-bromo-3-methylbut-2-ene.

6. The method of claim 5, wherein the amount of beta-acid (3) in the mixture of beta-acids is limited.

7. The method of claim 1, wherein the strong oxidation condition comprises concentrated sulfuric acid and hydrogen peroxide.

8. The method of claim 1, wherein the isomerization of step (d) is thermal isomerization catalyzed by alkali earth metals.

9. The method of claim 1, wherein the isomerization of step (d) is photo isomerization and the one or more diastereomers of tetrahydroisohumulone (9) are trans diastereomers.

10. The method of claim 1, further comprising performing an epimerization of the trans diastereomers of tetrahydroisohumulone (9) using one or more weak sterically non-hindered bases to produce cis and trans diastereomers of tetrahydroisohumulone (9).

11. The method of claim 10, wherein the one or more weak sterically non-hindered bases are selected from the group consisting of DMAP, DABCO, imidazole, isoquinoline, 4-picoline, pyridine, substituted pyridines, NMM, sodium acetate, and tetralkylammonium acetates.

12. A method of synthesizing a cis 3,4-dihydroxy-2-(3-methylbutanoyl)-5-(3-methylbutyl)-4-(4-methylpentanoyl) cyclopent-2-en-1-one ("KDT500") derivative comprising:
    a) performing an isomerization on a starting material comprising an alpha-acid derived from a hops $CO_2$ extract to produce a mixture of cis and trans diastereomers of isohumulone (12);
    b) isolating the cis diastereomers from the mixture of cis and trans diastereomers of isohumulone (12) by precipitating the trans diastereomers of isohumulone (12);
    c) performing a hydrogenation on the cis diastereomers of isohumulone (12) to produce a mixture of cis and trans diastereomers of tetrahydroisohumulone (9); and
    d) purifying KDT500 from the mixture of diastereomers of tetrahydroisohumulone (9) by one or more of a salt crystallization, counter-current chromatography (CCC) purification, and chiral chromatography; and
    e) performing a thermal epimerization of trans 3,4-dihydroxy-2-(3-methylbutanoyl)-5-(3-methylbutyl)-4-(4-methylpentanoyl)cyclopent-2-en-1-one in the presence of an alkaline earth metal.

13. The method of claim 12, wherein KDT500 derivative is a potassium salt of KDT500.

14. The method of claim 12, wherein the alpha-acid derived from a hops $CO_2$ extract is (−)-humulone (11).

15. The method of claim 12, wherein the isomerization is an alkaline thermal isomerization catalyzed by alkali earth metals.

16. The method of claim 12, wherein precipitating trans diastereomers of isohumulone is performed via a β-cyclodextrin complexation.

17. The method of claim 12, wherein the hydrogenation is performed in the presence of gaseous hydrogen ($H_2$) and palladium on carbon (Pd/C).

18. The method of claim 12, further comprising performing an epimerization of the trans diastereomers of tetrahydroisohumulone (9) using one or more weak sterically non-hindered bases to produce cis and trans diastereomers of tetrahydroisohumulone (9).

19. The method of claim 18, wherein the one or more weak sterically non-hindered bases are selected from the group consisting of DMAP, DABCO, imidazole, isoquinoline, 4-picoline, pyridine, substituted pyridines, NMM, sodium acetate, and tetralkylammonium acetates.

20. A method of synthesizing a cis 3,4-dihydroxy-2-(3-methylbutanoyl)-5-(3-methylbutyl)-4-(4-methylpentanoyl) cyclopent-2-en-1-one ("KDT500") derivative comprising:
    a) performing a photoisomerization on a starting material comprising an alpha-acid derived from a hops $CO_2$ extract to produce one or more cis diastereomers of isohumulone (12);
    b) performing a hydrogenation of the one or more cis diastereomers of isohumulone (12) to produce a mixture of cis and trans diastereomers of tetrahydroisohumulone (9);
    c) purifying KDT500 from the mixture of diastereomers of tetrahydroisohumulone (9) by one or more of a salt crystallization, CCC purification, and chiral chromatography; and
    d) performing a thermal epimerization of trans 3,4-dihydroxy-2-(3-methylbutanoyl)-5-(3-methylbutyl)-4-(4-methylpentanoyl)cyclopent-2-en-1-one in the presence of an alkaline earth metal.

21. The method of claim 20, wherein the KDT500 derivative is a potassium salt of KDT500.

22. The method of claim 20, wherein the KDT500 derivative is a potassium salt of KDT500.

23. The method of claim 20, wherein the alpha-acid derived from a hops $CO_2$ extract is (−)-humulone (11).

24. The method of claim 20, wherein the hydrogenation is performed in the presence of gaseous hydrogen ($H_2$) and palladium on carbon (Pd/C).

25. The method of claim 12, further comprising performing an epimerization of the trans diastereomers of tetrahydroisohumulone (9) using one or more weak sterically non-hindered bases to produce cis and trans diastereomers of tetrahydroisohumulone (9).

26. The method of claim 25, wherein the one or more weak sterically non-hindered bases are selected from the group consisting of DMAP, DABCO, imidazole, isoquinoline, 4-picoline, pyridine, substituted pyridines, NMM, sodium acetate, and tetralkylammonium acetates.

27. A method of preparing a cis 3,4-dihydroxy-2-(3-methylbutanoyl)-5-(3-methylbutyl)-4-(4-methylpentanoyl)cyclopent-2-en-1-one ("KDT500") derivative comprising performing a thermal epimerization of trans 3,4-dihydroxy-2-(3-methylbutanoyl)-5-(3-methylbutyl)-4-(4-methylpentanoyl) cyclopent-2-en-1-one in the presence of an alkaline earth metal.

* * * * *